United States Patent [19]

Carlsson et al.

[11] Patent Number: 5,124,441

[45] Date of Patent: Jun. 23, 1992

[54] THERAPEUTICALLY ACTIVE COMPOUND AND ITS USE

[75] Inventors: Jan P. E. Carlsson; Rolf E. A. V. Axén, both of Upsala, Sweden

[73] Assignee: Pharmacia Aktiebolag, Upsala, Sweden

[21] Appl. No.: 728,392

[22] Filed: Apr. 29, 1985

Related U.S. Application Data

[63] Continuation of Ser. No. 498,005, May 25, 1983, abandoned, which is a continuation of Ser. No. 364,674, Apr. 2, 1982, abandoned.

[30] Foreign Application Priority Data

Apr. 6, 1981 [SE] Sweden .................. 8102193

[51] Int. Cl.⁵ .................. C07H 15/24; C07H 17/02; C07J 17/00; A01N 43/04
[52] U.S. Cl. .................. 536/6.1; 536/6.4; 536/17.2; 536/17.3; 536/17.4; 536/17.5; 536/17.7; 536/17.6; 536/17.8; 536/17.9; 514/192; 514/193; 546/294; 548/165; 548/166
[58] Field of Search .................. 536/17.1–17.9, 536/6.1, 6.4; 514/34, 707, 155, 192–197; 544/17; 546/294; 548/165, 166

[56] References Cited

FOREIGN PATENT DOCUMENTS 55-22657 2/1980 Japan .

Primary Examiner—Nathan M. Nutter
Attorney, Agent, or Firm—Fred Philpitt

[57] ABSTRACT

Therapeutically active organic compound exhibiting at least one group comprising a structure —S'—S"—R, wherein the group —S"—R is defined by R being an organic group comprised in a physiologically acceptable compound H—S"—R obtainable by the splitting of the disulfide bridge —S'—S"— in said structure, in which compound H—S"—R the sulfur atom S" is bound to a carbon atom in a heterocyclic aromatic ring in R having a configuration being such that the compound H—S"—R, while maintaining physiological acceptability, is stabilized, by tautomerism or resonance involving the sulfur atom S" bound to R, so as to be mainly excluded from reaction involving thiol disulfide exchange; S' being bound to an aliphatic carbon atom; and said compound, in addition to the group or groups comprising the structure —S'—S"—R, consisting of a residue of a therapeutically active organic base compound of non-polypeptide structure bound to S'.

The invention also relates to a method of modifying a therapeutically active, organic compound of non-polypeptide structure by introducing a structure —S'—S"—R according to above; a method of treating diseases by administration of a compound according to the invention and also to a pharmaceutical composition containing at least one compound according to the invention.

5 Claims, No Drawings

THERAPEUTICALLY ACTIVE COMPOUND AND ITS USE

This is a continuation of application Ser. No. 498,005, filed May 25, 1983 and now abandoned, and which application is a continuation of application Ser. No. 364,674 filed Apr. 2, 1982 and now abandoned, and the benefits of 35 USC 120 are claimed relative to them.

The present invention relates to a therapeutically active organic compound which exhibits at least one group comprising a structure —S'—S"—R.

Derivatives of 6-mercaptopurine and 2-amino-6-mercaptopurine, which are both cell growth inhibitors, are disclosed in U.S. Pat. No. 3,400,125. This publication describes mercapto groups derivatized to —S'—S"—R', where R' is lower alkyl, aryl, aralkyl, di-(lower alkyl)-amino, cyclic secondary amino or trichloromethyl. The disulfide bond in those derivatives would be expected to participate in thiol disulfide exchange reactions. In this type of reaction a compound containing thiol groups reacts with the disulfide derivatives releasing 6-mercaptopurine and 2-amino-6-mercaptopurine respectively (which are both cell growth inhibitors). The sulfur atom of the thiol group of the compound is thereby bound to the sulfur atom of the residue —S—R'.

Compounds of U.S. Pat. No. 3 400 125 may thus lead to a direct release of a therapeutically active thiol compound from their disulfide derivatives. On the other hand, the present invention is based on binding in vivo of a therapeutically active thiol compound. This binding takes place via a thiol disulfide exchange reaction. According to the invention this is accomplished by a compound mentioned in the introductory part wherein the group —S"—R is defined by R being an organic group comprised in a physiologically acceptable compound H—S"—R obtainable by the splitting of the disulfide bridge —S'—S"— in said structure, in which compound H—S"—R the sulfur atom S" is bound to a carbon atom in a heterocyclic aromatic ring in R, having a configuration being such that the compound H—S"—R, while maintaining physiological acceptability, is stabilized, by tautomerism or resonance involving the sulfur atom S" bound to R, so as to be mainly excluded from reaction involving thiol disulfide exchange; S' being bound to an aliphatic carbon atom; and said compound, in addition to the group or groups comprising the structure —S'—S"—R, consisting of a residue of a therapeutically active organic base compound of non-polypeptide structure bound to S'.

(The different sulfur atoms have been labeled with ' and " for distinguishing of sulfur atoms directly bound to different molecular moieties.)

Thus, one common feature for the groups R is that, in thiol disulfide reactions, they produce thiol compounds, which are stabilized to inert compounds by resonance or tautomerism, i.e. to compounds which substantially do not participate in thiol disulfide exchange reactions. However, the other moiety of the molecule, which corresponds to the residue of the base compound forms a new disulfide and may thus participate in further such reactions.

There are present many thiol compounds belonging to the group of proteins in mammals including humans. These thiol compounds may participate in thiol disulfide exchange reactions with derivatives according to the invention. In this way another disulfide is formed, which may participate in further such exchange reactions transferring to the thiol compounds the residue, which is related to the base compound.

Usually, antibacterial compounds, like penicillins, cephalosporins and tetracyclines, are excreted or otherwise eliminated relatively quickly in mammals. By modifying such compounds to a derivative according to the invention the duration of their activity may be essentially prolonged.

Advantageous effects, which are based on repeated thiol disulfide exchange reactions in vivo may be achieved also by other types of therapeutically active compounds modified according to the invention.

In general only one structural unit —S'—S"—R is present in the therapeutically active compound, but there are compounds with two, three or even more of these units.

The structures —S'—S"—R in the therapeutically active compound are always bound to a primary, secondary or tertiary aliphatic carbon atom, to which no atoms other than carbon and hydrogen are bound, i.e. the structure —S'—S"—R is preferably bound according to the formulas

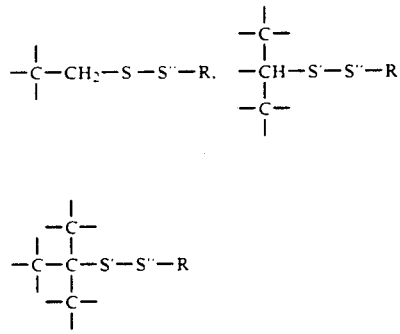

In general the structure —S'S"—R is bound to an aliphatic carbon in a hydrocarbon chain, which may be straight, branched or cyclic and which also may be substituted. The structure —S'—S"—R may e.g. be bound to an aliphatic carbon atom in a group according to the formula —A—S'—S"—R, where A is a straight, branched or cyclic hydrocarbon chain consisting of e.g. 1 to 10 carbon atoms. The chain may e.g. optionally be substituted with 1 to 3 hydroxyl groups and may optionally be broken by 1 to 3 oxygen or sulfur atoms, preferably at most one other atom except carbon and hydrogen is bound to the same carbon atom in the group A.

The therapeutically active compound may e.g. have the structure —S'—S"—R positioned in a group of the formula —X—A—S'—S"—R, which group is comprised in a compound of the general formula $$T_1-X-A-S'-S''-R \tag{I}$$

where
a) R, S' and S" have the meanings given above
b) A has the meanings given above
c) X is
   1) a direct link to an amino- or amide-nitrogen atom or a carbon atom in $T_1$
   2) the group —CO— bound to a nitrogen or oxygen atom in $T_1$
   3) the group —CO—O— bound to a carbon or nitrogen atom in $T_1$ or 4) the atom —O— bound to a carbon atom in $T_1$
and d) $T_1$ is a residue of a preferably therapeutically active organic compound of non-polypeptide structure and of the formula T= i) $T_1$—X—H (II)

ii) $T_1$—X—A—H (III) or iii) $T_1$—X—A—S'—H (IV')

where X, A and S' have the meanings given above.

Compounds according to the invention may be synthesized by methods, e.g. known per se, for transforming thiol groups to disulfide groups.

Preferably a compound containing thiol groups, e.g. according to IV above, is reacted with a symmetric disulfide of the formula

R—S—S—R (V)

where R has the meanings given above. In this reaction a considerable excess of disulfide is used.

Many therapeutically active thiol compounds (e.g. according to the structure IV above), which do not have polypeptide structure and which can be transformed to compounds according to the invention, are previously known, e.g. from the patent literature.

Examples of such known compounds are blood pressure regulators, antiinflammatory substances, antirheumatics, antimicrobials and cell growth regulators etc. (see e.g. U.S. Pat. Nos. 4,048,430, 4,144,271, 4,199,512, 4,211,786 and 4,220,791, German Offenlegungschriften 2 339 953 and 2 941 288 and European patent publication 0 008 058).

Starting with a compound, according to formula (II) above, containing a nitrogen atom comprised in an amino group or an amide group, which is able to be present in alkylated form while exhibiting therapeutical activity, X, in the group

—X—A—S'—S"—R.

may for instance be a direct link to said nitrogen atom.

A direct bond, formed by alkylation of the nitrogen atom of an amino group, is introduced e.g. by a) substitution by the aid of a halogen compound b) addition to a carbon-carbon double bond, particularly a polarized one as in e.g. alpha, beta unsaturated carboxylic acids and their esters c) reduction of condensation products formed by reactions of amines with carbonyl groups, for instance by hydrogenation and d) Mannich condensation, i.e. a condensation in which a carbonyl compound together with a primary or secondary amine condenses at a carbon atom having a reactive hydrogen. One particular carbonyl compound is formaldehyde.

Direct binding between an alkyl halide and a primary or secondary nitrogen in an amide group is carried out e.g. in an inert solvent containing sodium amide. Structures like —CO—NH—A— are more easily formed from their corresponding carboxylic acids compared to methods starting with compounds of the structure —CO—NH$_2$. Carboxylic acids may be prepared from amides by acid or alkaline saponification, preferably according to Bouveault. Different methods for synthesis of amides from carboxylic acids are given below.

Starting with a compound, according to formula (II) above, containing a nitrogen atom comprised in an amino group, which is able to be present in acylated form while exhibiting therapeutical activity, X, in the group —X—A—S'—S"—R, may for instance be —CO— bound to said nitrogen atom. This type of a directed acyl-amide bond may be synthesized in many ways. Usually compounds having reactive carboxy groups are used. Examples of such compounds are esters, e.g. p-nitro-phenyl esters, or anhydrides particularly unsymmetrical, e.g. unsymmetrical anhydrides formed by reaction between a carboxylic acid and the isobutyl ester of chloroformic acid, or compounds like acyl halides (—CO—Cl) and acyl azides (—CON$_3$). One particularly preferred activated structure is the O-acyl-isoureido structure, which is formed by reaction of carboxylic acids with carbodiimides particularly dicyclohexyl-carbodiimide. Lactones are another type of activated carboxy compounds. Thiollactones constitute a useful type of lactones, which are able to simultaneously amidate and thiolate an amino group. One well-known reagent is N-acetyl-homocysteine-thiollactone.

Starting with a compound, according to formula (II) above, containing an oxygen atom comprised in an hydroxyl group, which can be present in alkylated or acylated form exhibiting therapeutical activity, X, in the group —X—A—S'—S"—R mentioned above, may for instance be a direct link or —CO— bound to said oxygen atom.

Direct binding of carbon atom in the group A to an oxygen atom in a hydroxyl group leads to etherification. The most common type of etherification is Williamson's synthesis for ethers. This type is also useful for phenyl ethers.

In this connection a suitable method is condensation of epichlorohydrin with alkoxides and phenolates, which is controlled so as to result in a product having an epoxy structure. Such a structure may then be used for incorporation of sulfur essential for the invention. This incorporation of sulfur is possible via e.g. consecutive reactions like treatment with sodium thiosulfate, reduction to thiol and finally reaction with a symmetric and reactive disulfide. Bisepoxides and polyepoxides may be used analogously.

A certain type of ethers are acetals and ketals, which are synthesized by condensation of alcohols with aldehydes or ketones. This type of condensation makes use of acid catalysts e.g. hydrochloric acid, p-toluenesulfonic acid or cation-exchange resins. Another method is the binding of alcohols to vinyl groups. One embodiment of particular interest makes use of 2,3-epoxypropanal for formation of the structure —X—A—S'—S"—R by the epoxy route.

There are large number of methods available for acylation of hydroxyl groups. Esterification with carboxylic acids promoted by dicyclohexyl carbodiimide as condensation agent and 4-dimethylaminopyridine as a suitable catalyst is a method offering mild reaction conditions. N, N'-carbonyldiimidazol is another example of a condensation agent offering mild conditions. These condensation agents may be used for coupling of e.g. 3-(2-pyridinedithio)-propionic acid. Other examples of acylation reagents are hydroxysuccinimidyl esters of carboxylic acids. The above reagents may be used for binding e.g. glycidic acids in ester bonds, whereafter the epoxy structure can be used for introduction of functional groups containing sulfur as given above. A quite different method for introducing glycidyl ester structures is to react a hydroxylic compound with an X-halo fatty acyl halide e.g. chloroacetyl chloride. After isolation the X-chloro fatty acid ester is reacted with an aldehyde or a ketone according to Darzen. The latter reaction is run at alkaline pH. Thiooctanoic acid e.g. in oxidized form may be bound by the above acylation reactions, whereafter its disulfide group may be transformed to two reactive disulfides. Starting with a compound, according to formula (II) above, containing a carboxy group, which is able to be present in esterified form while exhibiting therapeutical activity, the compound formed may for instance comprise the structure —CO—O—A—S'—S"—R. Syntheses of ester structures has been indicated above. Re-esterification reaction by alcoholysis may also be applied, e.g. by the use of glycidol.

In order to obtain a therapeutically active compound comprising the group —X—A—S'—S"—R also methodologies may be selected, which mean a simultaneous binding together of several functional groups to a suitable structure of —X—A—. In this connection one especially useful way of synthesis in alpha-addition to isocyanides by immonium ions and carboxylate ions followed by rearrangement according to Ugi. Thus this method involves a simultaneous condensation of a carbonyl function, amino function, carboxy function and isocyanide function.

Sulfonic acid amides are prepared analogously to those mentioned for carboxylic acid amides.

All the above methods often require a selective introduction and removal of protecting groups. Otherwise the wrong functional groups may be derivatized. A large number of such protecting groups are known to the organic chemists.

A therapeutically active compound containing an amino group may be directly transformed to a compound according to the invention. This may preferably be carried out by reacting the starting compound with a compound of the formula

R—S'—S"—A—Z  (VI)

where R has the same meanings as given above, preferably 2-pyridyl, 5-nitro-2-pyridyl, 4-pyridyl, 5-carboxy-2-pyridyl, the N-oxide of any of these four groups, especially 2-pyridyl-N-oxide, or 2-benzothiazolyl, A has the same meanings as given above and Z has the structure

or acid addition salts thereof, where n is 2 or 3, R is identical with and has the same meanings as given above and Y is methyl or ethyl. Preferably A is —CH$_2$—CH$_2$— and Z is

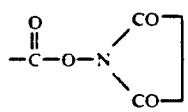

Preparation of compounds according to formula (VI), where R is 2-pyridyl, 5-nitro-2-pyridyl, 4-pyridyl and 5-carboxy-2-pyridyl, has been described in U.S. Pat. No. 4,149,003. Synthesis of the corresponding N-oxides and compounds of formula VI, where R being 2-benzothiazolyl is carried out analogously (compare "German Offenlegungsschrift" 2 917 001).

The reaction between the starting amino compound and the compound of formula (VI) is carried out in organic milieu, preferably with methanol or ethanol as a solvent and triethylamine as a base catalyst.

This reaction can be exemplified by reacting a therapeutically active compound having a primary amino group (T$_2$—NH$_2$) with N-succinimidyl 3-(2-pyridyldithio) propionate. This reaction is represented as follows:

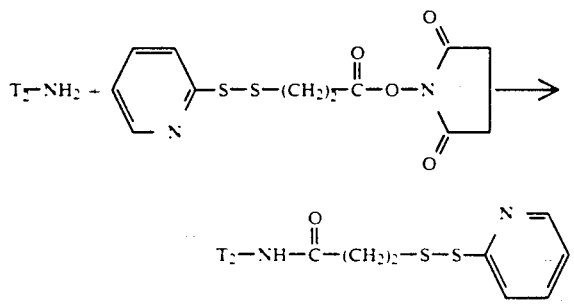

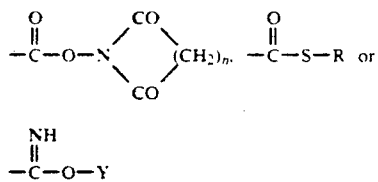

Examples are given below of therapeutically active compounds having no thiol groups, but which may be transformed to compounds according to the invention. Such examples are:

Known cytostatic compounds comprising one or more primary or secondary amino groups. Examples of such cytostatics are melfalan and antracyclineglycosides as daunorubicin and doxorubicin.

Antimicrobials as penicillins and cephalosporins, both types having an amino group as in amoxicillin, ampicillin, bakampicillin, pivampicillin, cephalexin, cephradin etc. Other antimicrobials are tetracyclines as chlorotetracycline, doxycycline, metacycline, oxytetracycline and lymecycline. Moreover, framycetin, kanamycin and tobramycin may be mentioned. There are also known compounds with a weak therapeutic activity like 6-aminopenicillanic acid (6-APA) and 7-aminocephalosporanic acid (7-ACA) and their analogues modified in their 2- and 3-position respectively, by methods known per se. 6-APA, 7-ACA and the above mentioned analogues may be transformed to derivatives according to the invention, e.g. by reacting the 6-amino or 7-amino group, respectively, with a compound of formula (VI).

Due to their lack of anti-microbial effect 6-APA and 7-ACA are normally not classified as a penicillin and a cephalosporin respectively.

According to the invention it is also of interest to modify sulfa compounds having a primary amino group e.g. sulfafurazole, sulfamethizole, sulfaisodimidine, sulfamethoxazole, sulfamoxole, sulfadimethoxine, sulfamethoxypyridazine and sulfamethoxydiazine.

There are also known may other therapeutically active compounds which may be modified according to the invention. Of course, then should not be modified at structural units having profound effects on the therapeutical activity.

A derivative according to the invention may be administered in those forms which are useful for the therapeutically active base compound. However, the derivative is preferably used in the form of solutions or suspensions for injection or infusion.

The dosage varies with the choice of compound and desired therapeutic effect. The dosage of a number of derivatives may, according to the invention, be increased in comparison (estimated on molar basis) with the dosage of the base compounds due to increased tolerance for the new compounds. In other cases the dosage may be lower than the dosage of base compound still with obtaining the corresponding therapeutic effect due to a lower decomposition rate.

Free thiol groups are often reactive and may react with other groups in the molecule, be oxidized or react in another manner, leading to instability in the compound. However, in the derivative, according to the invention, the —S"—R functions as protecting group for the thiol group —S'—H, which leads to increased stability and therewith improved storage properties.

EXAMPLE 1

Daunorubicin-2-pyridyl disulfide derivative

Preparation 120 mg daunorubicin hydrochloride (daunomycin hydrochloride) was dissolved in 24 ml methanol (99.5% v/v). 2.4 ml triethylamine (161 mg/10 ml methanol) was added, whereafter 6.6 ml N-succinimidyl-(2-pyridylditio)-propionate (SPDP from Pharmacia Fine Chemicals AB, Uppsala, Sweden) (32 mM in 99.5% v/v methanol) was added. After vigorous stirring, the reaction mixture was left at +25° C. for 60 minutes, and then at +4° C. for 20 hours and a dark red product was crystalized. The product was isolated through filtration, washed with ice-cooled (0° C.) methanol and dried.

Infra-red spectroscopy, mass-spectrometry, elementary analysis, among others, showed that the product was analytically pure daunorubicin-2-pyridyl disulfide-derivative corresponding with the formula

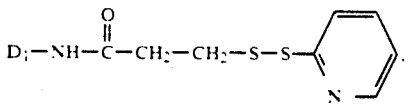

where $D_1$—NH is a residue of daunorubicin.

Analysis: Calculated for $C_{35}O_{11}H_{36}N_2S_2$: C 57.98%; H 5%; N 3.87%; S 8.85%. Found: C 57.98%; H 4.96%; N 3.83%; S 8.55%.

Investigation of pharmacologic qualities a) Anti-tumor effects on rats

Female rats, type BN/NF with a body weight of 250–500 g were used as test animals. The rats were inoculated Day 0, intraperitoneally with 0.5 ml of a suspension containing 1.5 10⁶ cells of type "PW 13-11-T 14" virus-induced kidney sarcoma. (The tumor was kept alive in the laboratory through a series of transplations in syngenic WF-rats.) 24 rats were treated in this manner.

Day 1 after inoculation, the rats were treated as follows:

Group A: 6 rats with 4 ml 0.1 m Na-phosphate pH 7.0.
Group B: 6 rats with 4 ml daunorubicin hydrochloride, 0.26 mg/ml dissolved in 0.1M Na-phosphate pH 7.0.
Group C: 12 rats with 4 ml daunorubicin-2-pyridyl disulfide derivative prepared according to the above, 0.26 mg/ml in 0.1M Na-phosphate pH 7.0.

The result is given in the table below:

TABLE 1

| Treatment | Number surviving animals after |||||| 
| | 5 | 10 | 15 | 20 | 25 | 30 days |
| Group A (6) (control) | 5 | 0 | 0 | 0 | 0 | 0 |
| Group B (6) (daunorubicin hydrochloride) | 4 | 2 | 0 | 0 | 0 | 0 |
| Group C (12) (daunorubicin-2-pyridyl-disulfide derivative) | 12 | 11 | 6 | 2 | 1 | 1 | b) Toxicity in mice

Male mice were used as test animals, type NMRI with a body weight of 25±2 g. 3 groups of 8 mice each were treated by i.p. injection as follows:

Group A: 0.5 ml 0.1M Na-phosphate pH 7.0.
Group B: 0.5 ml daunorubicin hydrochloride, 0.6 mg/ml in 0.1M Na-phosphate pH 7 (lethal dose).
Group C: 0.5 ml daunorubicin-2-pyridyl disulfide derivate, prepared according above, 0.6 mg/ml in 0.1M Na-phosphate pH 7.

All of the mice survived in groups A and C, while the average survival-rate and the median survival-rate in group B was 8.4 resp. 8 days.

EXAMPLE 2

Doxorubicin-2-pyridyldisulfide derivative

Synthesis 120 mg doxorubicin hydrochloride (Adriamycin$^R$) was dissolved in 24 ml methanol (99.5% v/v), 2.4 ml triethylamine (161 mg/10 ml methanol 99.5% v/v) was added followed by addition of 6.5 ml SPDP, 32 mM in 99.5% methanol. After vigorous stirring, the mixture was left at ±25° C. for 60 minutes and then at ±4° C. for 20 hours, where a dark red product as crystalized. The product was isolated through filtration, washed with ice-cooled (0° C.) methanol and dried. Infra-red spectroscopy, mass-spectrometry, and elementary analysis, among others, showed that the product was analytically pure doxorubicin-2-pyridyl disulfide corresponding with the formula

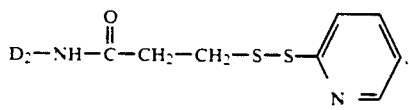

where $D_2$—NH is a residue of doxorubicin.

Investigation of the effect on human gliom cells

Malignant gliom cells (251 MG) were incubated in 5 ml Eagles MEM medium (10% v/v fetal serum) in petri dishes (360 000 cells/petri dish) at +37° C. for 24 hours. After this, 100 μl of different solutions according to table 2 below, were added to the petri dishes, which were incubated at +37° C. for additional 4×24 hours.

The cells were released by trypsination and counted separately by use of a celloscope in the different petri dishes. Table 2 below gives the result.

TABLE 2

| Solution | Cells per petri dish after 5 days and nights ||
| | Petri dish 1 | Petri dish 2 |
| Physiological phosphate | 776 000 | 840 000 |

TABLE 2-continued

| Solution | Cells per petri dish after 5 days and nights | |
|---|---|---|
| | Petri dish 1 | Petri dish 2 |
| buffer pH 6.0 | | |
| 0.25 mM doxorubicin hydrochloride in physiol. phosphate buffer pH 6.0 | 397 000 | 390 000 |
| 0.25 mM doxorubicin-2-pyridyl disulfide derivative (synthesized as above) in physiol phosphate buffer pH 6.0 | 380 000 | 397 000 |

EXAMPLE 3

Penicillin-2-pyridyl disulfide derivative

Synthesis 50 mg 6-aminopenicillinic acid was mixed with 2 ml of methanol. 25 mg triethylamine was added and the mixture was shaken until all the material was dissolved. 75 mg SPDP was added and the reaction mixture was stirred for 90 minutes at +25° C. The product was used in the below testing.

Antimicrobial activity

Staphylococcus aureus (stamm 8325-4) was cultured on blood agar. An amount giving a weak cloudy solution was transferred by an inoculating needle to 10 ml sterile, phosphate buffered saline.

A blood agar plate was smeared with the bacteria suspension and dried for 10 minutes. Thereafter wells of 50 μl were punched in the plate. To each well was added 50 μl solution of either the penicillin derivative (from above), penicillin G (as reference) or relevant blanks. The blanks were different compounds which were present in the reaction mixture above. The added solution was made from sterile phosphate buffered saline. The solutions of the different compounds were 10, 1, 0.1 and 0.01 μg/ml. The plates were incubated for 24 hours at 37° C. Visual inspection of the inhibition zones around the wells showed that the penicillin-2-pyridyl disulfide derivative had an antimicrobial activity comparable to that of penicillin G.

EXAMPLE 4

Thiolated daunorubicin

Synthesis 120 mg of daunorubicin hydrochloride (daunomycin hydrochloride) was dissolved in 24 ml of methanol (99.5% v/v). 2.4 ml triethylamine (161 mg/10 ml methanol) was added and followed by 6.6 ml N-succinimidyl 3-(2-pyridyldithio)-propionate (SPDP from Pharmacia Fine Chemicals AB, Uppsala, Sweden) (32 mM in 99.5% v/v methanol). After vigorous stirring the reaction mixture was left for 40 minutes at +25° C. and 0.1 ml 0.2M dithiothreitol in distilled water was added. The mixture was left for another 1 200 minutes at +4° C. where a red precipitate was formed. The product was isolated by filtration, washed with ice-cold (0° C.) methanol and dried. IR-spectroscopy, masspectrometry, elementar analysis etc. was in agreement with a compound of the formula

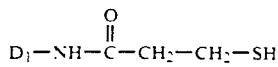

$$D_1-NH-\overset{O}{\underset{\|}{C}}-CH_2-CH_2-SH$$

where $D_1$—NH is a residue of daunorubicin.

This thiolated daunorubicin was shown to have antitumour activity on human gliom cells. This test was carried out as in example 2. The thiolated daunorubicin is able to be released in vivo when the compound of example 1 is administered to mammals.

EXAMPLE 5

Thiolated doxorubicin

Synthesis 120 mg doxorubicin hydrochloride (Adriamycin$^R$) was dissolved in 24 ml methanol (99.5% v/v). 2.4 ml triethylamine (161 mg/10 ml methanol (99.5% v/v) was added followed by 6.5 ml SPDP, 32 mM in 99.5% v/v methanol. After vigorous stirring the mixture was left for 40 minutes at +25° C. and 0.1 ml 0.2M dithiothreitol in distilled water was added subsequently. The mixture was shaken and left for another 1 200 minutes at +4° C. and a red precipitate was formed. The product was isolated by filtration, washed with ice-cold (0° C.) methanol and dried. IR-spectroscopy, masspectrometry, elementary analysis agreed with analytically pure thiolated doxorubicin of the formula

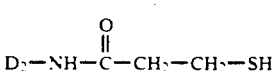

$$D_2-NH-\overset{O}{\underset{\|}{C}}-CH_2-CH_2-SH$$

where $D_2$—NH is a residue of doxorubicin.

This thiolated doxorubicin was shown to have antitumour activity on human gliom cells. Such tests were carried out as in example 2. This thiolated doxorubicin is able to be released in vivo when the derivative of example 2 is administrated to mammals.

We claim:

1. Therapeutically active compound having the formula

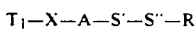

$$T_1-X-A-S'-S''-R$$

wherein

R is 2-benzothiazolyl, 2-pyridyl, 5-nitro-2-pyridyl, 4-pyridyl, 5-carboxy-2-pyridyl or the N-oxide of any of the last mentioned four groups, S' is bound to an aliphatic carbon atom, A is a straight, branched or cyclic hydrocarbon chain of 1-10 carbon atoms which is unsubstituted or substituted with 1-3 hydroxyl groups and which is non-broken or broken by 1-3 oxygen or sulfur atoms, at most one atom other than carbon and hydrogen being bound to one and the same carbon atom in A, $T_1$ is a residue of an organic compound $R_1$—X—H containing a primary or secondary amino group, said X in $T_1$—X—H being a direct link to a nitrogen atom of said amino group and said organic compound being selected from the group consisting of melfalan, antracyclineglycosides, penicillins, cephalosporins, 6-aminopenicillanic acid and its analog modified in the 2-position, and 7-aminocephalosporanic acid and its analog modified in the 3-position, and said X in $T_1$-—A—S'—S''—R is a direct link or the group —CO— bound to a nitrogen atom of said amino group in $T_1$—X—H.

2. Therapeutically active compound according to claim 1 wherein $T_1$—X—H is an antracyclineglycoside.

3. Therapeutically active compound according to claim 1 wherein $T_1$—X—H is daunorubicin.

4. Therapeutically active compound according to claim 1 wherein $T_1$—X—H is doxorubicin.

5. Therapeutically active compound according to claim 1 wherein $T_1$—X—H is a penicillin including 6-amino-penicillanic acid and its analogues modified at the 2-position.

* * * * *